(12) United States Patent  (10) Patent No.: US 7,708,776 B1
Blain et al.  (45) Date of Patent: May 4, 2010

(54) INTERVERTEBRAL DISK REPLACEMENT SYSTEM AND METHODS

(75) Inventors: Jason Daniel Blain, San Diego, CA (US); Keith Valentine, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 10/346,695

(22) Filed: Jan. 16, 2003

Related U.S. Application Data

(60) Provisional application No. 60/349,626, filed on Jan. 16, 2002.

(51) Int. Cl.
*A61F 2/44* (2006.01)

(52) U.S. Cl. .................. 623/17.14; 623/17.15; 623/908; 606/279

(58) Field of Classification Search .............. 623/17.11, 623/17.14, 17.15, 19.12, 20.22, 21.13, 21.16, 623/23.4; 606/61
See application file for complete search history.

(56) References Cited

U.S. PATENT DOCUMENTS

| | | | |
|---|---|---|---|
| 3,875,595 A | 4/1975 | Froning | |
| 4,309,777 A | 1/1982 | Patil | |
| 4,349,921 A | 9/1982 | Kuntz | |
| 4,401,112 A | 8/1983 | Rezaian | |
| 4,501,269 A | 2/1985 | Bagby | |
| 4,553,273 A | 11/1985 | Wu | |
| 4,554,914 A | 11/1985 | Kapp et al. | |
| 4,627,853 A | 12/1986 | Campbell et al. | |
| 4,636,217 A | 1/1987 | Ogilvie et al. | |
| 4,678,470 A | 7/1987 | Nashef et al. | |
| 4,714,469 A | 12/1987 | Kenna | |
| 4,743,256 A | 5/1988 | Brantigan | |
| 4,743,259 A | 5/1988 | Bolander et al. | |
| 4,759,766 A | 7/1988 | Buettner-Janz et al. | |
| 4,759,769 A | 7/1988 | Hedman et al. | |
| 4,834,757 A | 5/1989 | Brantigan | |
| 4,863,476 A | 9/1989 | Shepperd | |
| 4,863,477 A | 9/1989 | Monson | |
| 4,878,915 A | 11/1989 | Brantigan | |
| 4,932,975 A | 6/1990 | Main et al. | |
| 4,961,740 A | 10/1990 | Ray et al. | |
| 4,997,432 A | 3/1991 | Keller | |
| 5,015,247 A | 5/1991 | Michelson | |
| 5,026,373 A | 6/1991 | Ray et al. | |
| 5,055,104 A | 10/1991 | Ray | |
| 5,059,193 A | 10/1991 | Kuslich | |
| 5,062,850 A | 11/1991 | MacMillan et al. | |

(Continued)

FOREIGN PATENT DOCUMENTS

CA  1146301  5/1983

(Continued)

*Primary Examiner*—Brian E. Pellegrino
(74) *Attorney, Agent, or Firm*—Jonathan Spangler; Jay Bell (57) ABSTRACT

An improved total disc replacement system and related methods, wherein a pair of anchor plates, each adapted to engage a vertebral body, and a translating internal member are provided. The translating internal member boasts the ability to move or translate between the anchor plates without compromising the conformity of the interface between the translating internal member and the anchor plates. In a significant aspect, the anchor plates may be locked in place relative to one another after implantation to effect fusion between the vertebral bodies.

22 Claims, 5 Drawing Sheets

U.S. PATENT DOCUMENTS

| | | | |
|---|---|---|---|
| 5,071,437 A | 12/1991 | Steffee | |
| 5,122,130 A | 6/1992 | Keller | |
| 5,123,926 A | 6/1992 | Pisharodi | |
| 5,147,402 A | 9/1992 | Bohler et al. | |
| 5,192,327 A | 3/1993 | Brantigan | |
| 5,236,460 A | 8/1993 | Barber | |
| 5,258,031 A | 11/1993 | Salib et al. | |
| 5,263,953 A | 11/1993 | Bagby | |
| 5,290,312 A | 3/1994 | Kojimoto et al. | |
| 5,306,310 A | 4/1994 | Siebels | |
| 5,314,477 A | 5/1994 | Marnay | |
| 5,320,644 A | 6/1994 | Baumgartner | |
| 5,336,223 A | 8/1994 | Rogers | |
| 5,370,697 A * | 12/1994 | Baumgartner | 623/17.15 |
| 5,397,364 A | 3/1995 | Kozak et al. | |
| 5,401,269 A | 3/1995 | Buttner-Janz | |
| 5,417,975 A | 5/1995 | Lussi et al. | |
| 5,425,769 A | 6/1995 | Snyders, Jr. | |
| 5,425,773 A | 6/1995 | Boyd | |
| 5,439,684 A | 8/1995 | Prewett et al. | |
| 5,455,231 A | 10/1995 | Constantz et al. | |
| 5,464,439 A | 11/1995 | Gendler | |
| 5,480,442 A | 1/1996 | Bertagnoli | |
| 5,507,813 A | 4/1996 | Dowd et al. | |
| 5,507,816 A | 4/1996 | Bullivant | |
| 5,507,818 A * | 4/1996 | McLaughlin | 623/23.42 |
| 5,510,396 A | 4/1996 | Prewett et al. | |
| 5,522,899 A | 6/1996 | Michelson | |
| 5,534,029 A | 7/1996 | Shima | |
| 5,534,030 A | 7/1996 | Navarro et al. | |
| 5,549,679 A | 8/1996 | Kuslich | |
| 5,554,191 A | 9/1996 | Lahille et al. | |
| 5,556,431 A | 9/1996 | Buttner-Janz | |
| 5,562,738 A | 10/1996 | Boyd | |
| 5,585,116 A | 12/1996 | Boniface et al. | |
| 5,609,635 A | 3/1997 | Michelson | |
| 5,645,591 A | 7/1997 | Kuberasampath et al. | |
| 5,653,763 A | 8/1997 | Errico et al. | |
| 5,658,335 A | 8/1997 | Allen | |
| 5,665,122 A | 9/1997 | Kambin | |
| 5,674,294 A | 10/1997 | Bainville et al. | |
| 5,674,296 A | 10/1997 | Bryan | |
| 5,676,701 A | 10/1997 | Yuan | |
| 5,683,465 A | 11/1997 | Shinn | |
| 5,693,100 A | 12/1997 | Pisharodi | |
| 5,702,391 A | 12/1997 | Lin | |
| 5,702,450 A | 12/1997 | Bisserie | |
| 5,702,455 A | 12/1997 | Saggar | |
| 5,713,904 A | 2/1998 | Errico et al. | |
| 5,749,916 A | 5/1998 | Richelsoph | |
| 5,776,199 A | 7/1998 | Michelson | |
| 5,782,832 A | 7/1998 | Larsen | |
| 5,800,550 A | 9/1998 | Sertich | |
| 5,827,328 A | 10/1998 | Buttermann | |
| 5,888,227 A | 3/1999 | Cottle | |
| 5,893,889 A | 4/1999 | Harrington | |
| 5,928,284 A | 7/1999 | Mehdizadeh | |
| 6,019,762 A | 2/2000 | Cole | |
| 6,039,763 A | 3/2000 | Shelokov | |
| 6,045,579 A | 4/2000 | Hochshuler | |
| 6,063,121 A | 5/2000 | Xavier | |
| 6,086,613 A | 7/2000 | Camino | |
| 6,102,950 A | 8/2000 | Vaccaro | |
| 6,113,638 A | 9/2000 | Williams | |
| 6,139,579 A | 10/2000 | Steffee et al. | |
| 6,176,882 B1 | 1/2001 | Biedermann | |
| 6,183,517 B1 | 2/2001 | Suddaby | |
| 6,241,769 B1 | 6/2001 | Nicholson et al. | |
| 6,368,350 B1 | 4/2002 | Erickson | |

FOREIGN PATENT DOCUMENTS

| | | |
|---|---|---|
| EP | 0517030 | 5/1992 |
| WO | WO 0101893 A1 * | 1/2001 |

* cited by examiner

//www.w3.org/1999/xhtml">
INTERVERTEBRAL DISK REPLACEMENT SYSTEM AND METHODS

CROSS-REFERENCE TO RELATED APPLICATION

This application claims the benefit of the filing date under 35 USC 119(e) of provisional application entitled "Improved Disk Replacement System and Related Methods", Ser. No. 60/349,626 filed Jan. 16, 2002, and fully incorporated herein by reference.

BACKGROUND OF THE INVENTION

I. Field of the Invention

The present invention relates generally to spinal surgery and, more particularly, to improved total disc replacement systems and related methods.

II. Discussion of the Prior Art

In recent years, the area of total disc replacement has experienced proliferated growth and attention from the medical community. Known total disc replacement devices generally require some form of articulation or inherent flexibility in the device to permit a spine having the device to maintain its natural posture and range of motion as much as possible. Such devices typically include from between 2 and 4 separate components constructed from any number of materials, such as plastic, rubber, metal, ceramic and alloys. Generally speaking, these components include a pair of anchor plates for engagement with opposed vertebral body endplates and one or more internal components for simulating the intervertebral disc.

Known total disc replacement systems suffer disadvantages including the dislocation of the anchor plates from the vertebral end plates, over-distraction of the vertebral endplates during introduction, particulate wear and debris of the component parts, and a lack of conformity between the anchor plates and the internal components during use. Another disadvantage is that current designs do not permit a surgeon from undertaking post-implantation corrective measures such as interbody spinal fusion without first removing the entire total disc replacement system.

The present invention is directed at overcoming, or at least reducing the effects of, one or more of the problems set forth above.

SUMMARY OF THE INVENTION

The present invention solves the above-identified drawbacks with the prior art by providing a total disc replacement system including a pair of anchor plates and a translating internal member. In one aspect of the present invention, the translating internal member boasts the ability to move or translate between the anchor plates without compromising the conformity of the interface between the translating internal member and the anchor plates. More specifically, the translating internal member is maintained in either an unconstrained or semi-constrained fashion between the anchor plates such that the upper and lower surfaces of the internal member will not separate from the respective surfaces of the anchor plates during flexion/extension, lateral bending and/or axial rotation.

In an "unconstrained" embodiment, the first anchor plate is equipped with a generally concave receiving portion, the second anchor plate has a generally flat surface facing the generally concave receiving portion of the first anchor plate, and the translating internal member has a generally convex first surface for engaging with the generally concave receiving portion of the first anchor plate and a generally flat second surface for engaging with the generally flat surface of the second anchor plate. When implanted and anchored into the vertebral bodies, the generally flat surface of the internal member will be able to translate in any direction within the plane of the generally flat surface of the second anchor plate, while the convex-concave relationship between the first surface of the internal member and the receiving portion of the first anchor plate allow the first and second anchor plates to flex and extend relative to one another. In a significant aspect, all such motion can be accomplished without causing the convex-concave mating relation between the first anchor plate and the internal member to lose conformity. This is due to the fact that the substantially flat surfaces (on the second side of the internal member and the second anchor plate) are allowed to translate in a generally unencumbered fashion. In contradistinction, prior art devices which do not boast such an unconstrained translation (such as the ProDisc, which has an internal member with a substantially flat surface fixed relative to a substantially flat surface on an anchor plate) can suffer from at least one of: (a) a loss of conformity between the concave-convex mating surfaces; and/or (b) a shear force between the anchor plate and the vertebral body, which shear force may disadvantageously disrupt an otherwise sound and proper anchoring of the anchor plate to the vertebral body.

In a "semi-constrained" embodiment, the first anchor plate is equipped with a generally concave receiving portion, the second anchor plate has a generally flat surface facing the generally concave receiving portion of the first anchor plate and includes a post or rod element in the approximate center thereof, and the translating internal member has a generally convex first surface for engaging with the generally concave receiving portion of the first anchor plate, a generally flat second surface for engaging with the generally flat surface of the second anchor plate, and a recess formed in the approximate center of the generally flat surface for accepting the post or rod element of the second anchor plate. When implanted and anchored into the vertebral bodies, this embodiment functions in essentially the same manner as that described above with regard to the unconstrained embodiment, except that the post or rod element on the second anchor plate serves to limit the degree to which the internal member can translate relative to the second anchor plate. In a preferred embodiment, the post element and the recess are dimensioned such that the post element has a substantially smaller diameter than that of the recess, thereby allowing the post element to translate in all directions within the recess. The inventors believe that, in practice, this modest limitation on translation will nonetheless overcome and avoid the drawbacks of the prior art devices, preserving the conformity between the internal member and the anchor plates and minimizing (if not eliminating) any shear forces that would otherwise exist between the anchor plates and the vertebral bodies.

In another "semi-constrained" embodiment, the first anchor plate is equipped with a generally concave receiving portion, the second anchor plate has a generally flat surface facing the generally concave receiving portion of the first anchor plate and includes recess in the approximate center thereof, and the translating internal member has a generally convex first surface for engaging with the generally concave receiving portion of the first anchor plate, a generally flat second surface for engaging with the generally flat surface of the second anchor plate, and a post or rod element for engaging within the recess of the second anchor plate. When implanted and anchored into the vertebral bodies, this embodiment functions in essentially the same manner as that semi-constrained embodiment described above, except that the relative position of the post element and the recess is reversed.

In a further inventive aspect of the present invention, one or more of the anchor plates may be provided having a height that varies along a length of the anchor plate such that, when implanted, it forces the respective vertebral bodies into a non-parallel relationship. For example, for lumbar and cervical applications, varying the height of the anchor plate(s) (lower posteriorly and higher anteriorly) may advantageously facilitate a lordotic relationship between adjacent vertebral bodies as found naturally in those regions of the spine. In similar fashion, for thoracic applications, varying the height of the anchor plate(s) higher posteriorly and lower anteriorly may advantageously facilitate a kyphotic relationship between adjacent vertebral bodies as found naturally in that region of the spine.

Any number of fixation techniques or features may be employed to secure the anchor plates to the respective vertebral bodies. In a preferred embodiment, each anchor plate is equipped with a fin for securing the anchor plate to a vertebral endplate, such as by orienting the fin within a slot formed in the vertebral body. In a still further preferred embodiment, the fin may include a plurality of projections for resisting movement after implantation, thereby providing an additional anchoring mechanism to secure the anchor plates to the vertebral bodies.

In a still further important aspect of the present invention, the total disc replacement systems described herein or contemplated hereby may be provided such that the anchor plates may be locked in place relative to one another, thereby effectively accomplishing fusion between the adjacent vertebral bodies. In one embodiment, this is accomplished by providing each anchor plate with slots on either side of the internal assembly or internal member, wherein strut members can be introduced into the slots to effectively lock the relative position of the anchor plates. The feature is advantageous in that it provides the ability to undertake the post-implantation corrective measure of spinal fusion without first removing the entire total disc replacement system. Moreover, this design capitalizes on the fact that the anchor plates will likely have an extremely robust and secure engagement to the vertebral bodies, in that any corrective measure may well take place months, if not years, after the initial implantation of the total disc replacement device. By introducing the strut members between the securely engaged anchor members, fusion can be accomplished immediately and without fear of complications that sometimes occur during traditional fusion techniques.

BRIEF DESCRIPTION OF THE DRAWINGS

Other objects and advantages of the invention will become apparent upon reading the following detailed description and upon reference to the drawings in which.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In its most general sense, the present invention provides a total disc replacement system including a pair of anchor plates and a translating internal member. In a significant aspect of the present invention, the translating internal member boasts the ability to move or translate between the anchor plates without compromising the conformity of the interface between the translating internal member and the anchor plates. More specifically, the translating internal member is maintained in either an unconstrained or semi-constrained fashion between the anchor plates such that the upper and lower surfaces of the internal member will not separate from the respective surfaces of the anchor plates during flexion/extension, lateral bending and/or axial rotation.

Figure 1:
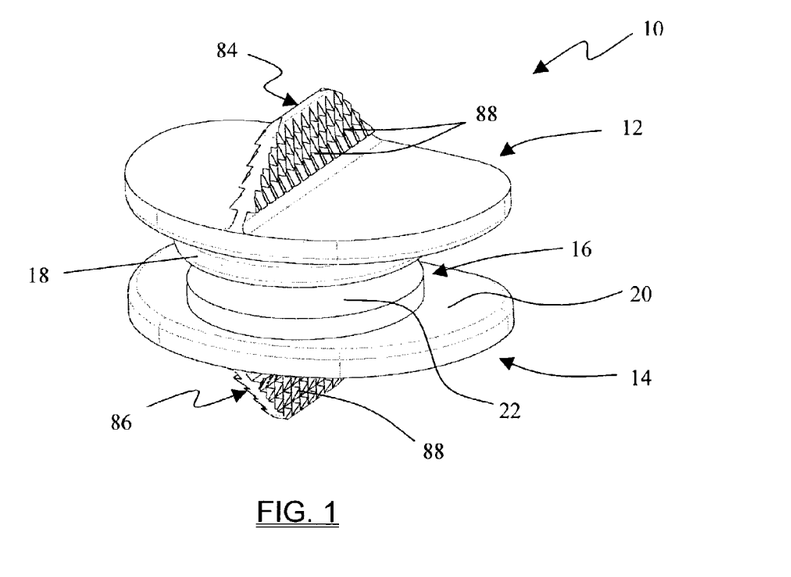
FIGS. 1-3 illustrate a total disc replacement system of "unconstrained" translational construction according to one aspect of the present invention.
Figure 2:
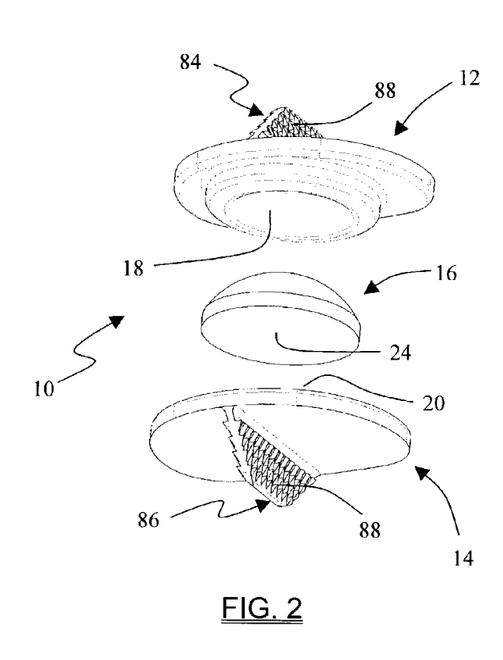
Figure 3:
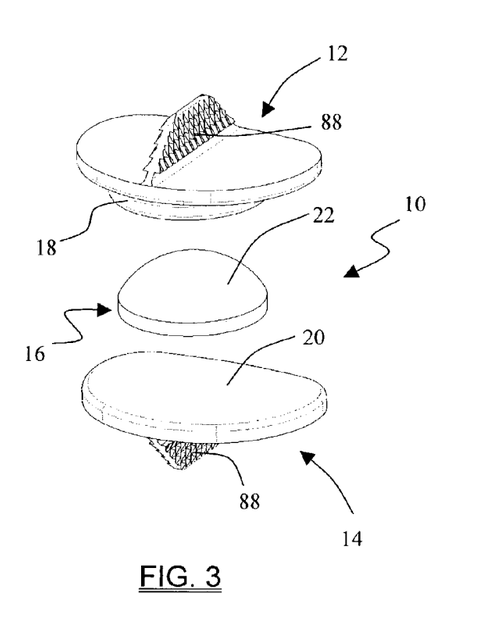

FIGS. 1-3 illustrate a total disc replacement (TDR) system 10 of "unconstrained" translational construction according to one aspect of the present invention. In this embodiment, the TDR system 10 includes a first anchor plate 12, a second anchor plate 14, and a translating internal member 16. The first anchor plate 12 is equipped with a generally concave receiving portion 18. The second anchor plate 14 has a generally flat surface 20 facing the generally concave receiving portion 18 of the first anchor plate 12. The translating internal member 16 has a generally convex first surface 22 for engaging with the generally concave receiving portion 18 of the first anchor plate 12 and a generally flat second surface 24 for engaging with the generally flat surface 20 of the second anchor plate 14. The first and second anchor plates 12, 14 described herein may be constructed from any number of suitable biocompatible compositions or materials, including but not limited to metallic compositions or alloys (such as Co—Cr—Mo), ceramics, or any of a variety of plastic compositions. The translating internal member 16 may similarly be constructed from any number of suitable biocompatible compositions or materials, including but not limited to polyethylene (such as ultra-high molecular weight polyethylene). Where beneficial, any of the components described herein as part of the present invention may be coated with any number of suitable compositions, such as zirconium oxide coating found in U.S. Pat. No. 5,037,438, the contents of which are hereby incorporated into this disclosure as if set forth in its entirety.

When implanted and anchored into the vertebral bodies, the generally flat surface 24 of the internal member 16 will be able to translate and/or rotate in any direction within the plane of the generally flat surface 20 of the second anchor plate 14, while the convex-concave relationship between the first surface 22 of the internal member 16 and the receiving portion 18 of the first anchor plate 12 allow the first and second anchor plates 12, 14 to experience flexion/extension, lateral bending and/or axial rotation relative to one another. In a significant aspect, all such motion can be accomplished without causing the convex-concave mating relation between the first anchor plate 12 and the internal member 16 to lose conformity. This is due to the fact that the substantially flat surfaces 20, 24 are allowed to translate and/or rotate in a generally unencumbered fashion. This advantageously prevents a loss of conformity between the concave-convex mating surfaces 18, 22, as well as prevents a shear force from developing between the anchor plates 12, 14 and the vertebral body which may otherwise occur (without such translational freedom between the internal member 16 and the second anchor plate 14) and disadvantageously disrupt an otherwise sound and proper anchoring of the anchor plates 12, 14 to the vertebral body.

Figure 4:
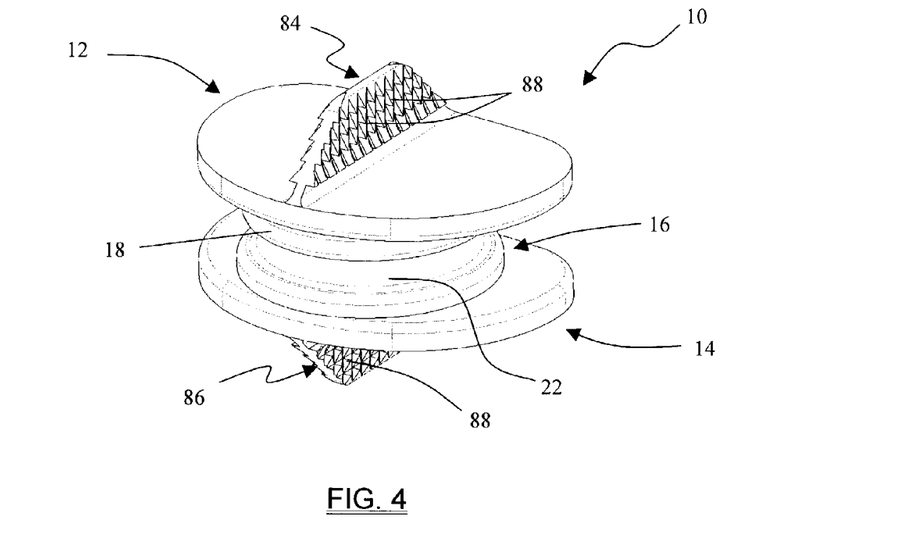
FIGS. 4-6 illustrate a total disc replacement system of "semi-constrained" translational construction according to another aspect of the present invention.
Figure 5:
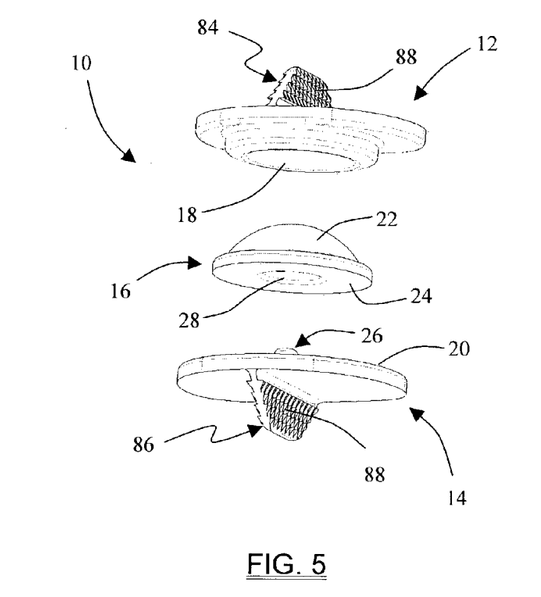
Figure 6:
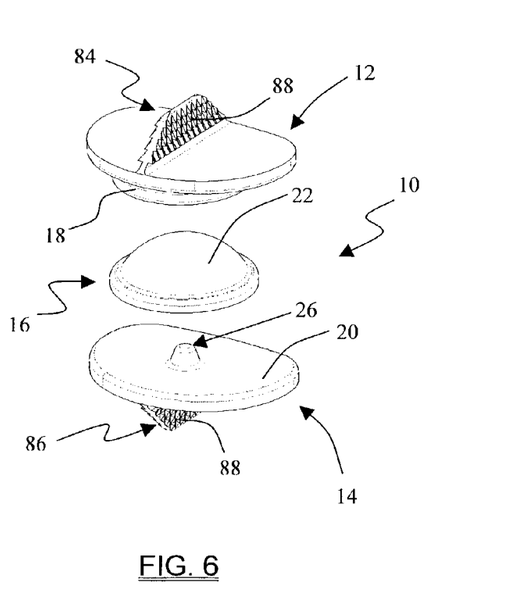

FIGS. 4-6 illustrate a TDR system 10 of "semi-constrained" translational construction according to another aspect of the present invention. In this embodiment, the first anchor plate 12 is equipped with a generally concave receiving portion 18. The second anchor plate 14 has a generally flat surface 20 facing the generally concave receiving portion 18 of the first anchor plate 12 and includes a post or rod element 26 in the approximate center thereof. The translating internal member 16 has a generally convex first surface 22 for engaging with the generally concave receiving portion 18 of the first anchor plate 12, a generally flat second surface 24 for engaging with the generally flat surface 20 of the second anchor plate 14. The translating internal member 16 also has a recess 28 formed in the approximate center of the generally flat surface 24 for accepting the post or rod element 26 of the second anchor plate 14. When implanted and anchored into the vertebral bodies, this embodiment functions in essentially the same manner as that described above with regard to the unconstrained embodiment, except that the post or rod element 26 on the second anchor plate 14 serves to limit the degree to which the internal member 16 can translate relative to the second anchor plate 14. In a preferred embodiment, the post element 26 and the recess 28 are dimensioned such that the post element 26 has a substantially smaller diameter than that of the recess 28, thereby allowing the post element 26 to translate in all directions within the recess 28. The inventors believe that, in practice, this modest limitation on translation will nonetheless overcome and avoid the drawbacks of the prior art devices, preserving the conformity between the internal member 16 and the anchor plates 12, 14 and minimizing (if not eliminating) any shear forces that would otherwise exist between the anchor plates 12, 14 and the vertebral bodies.

Figure 7:
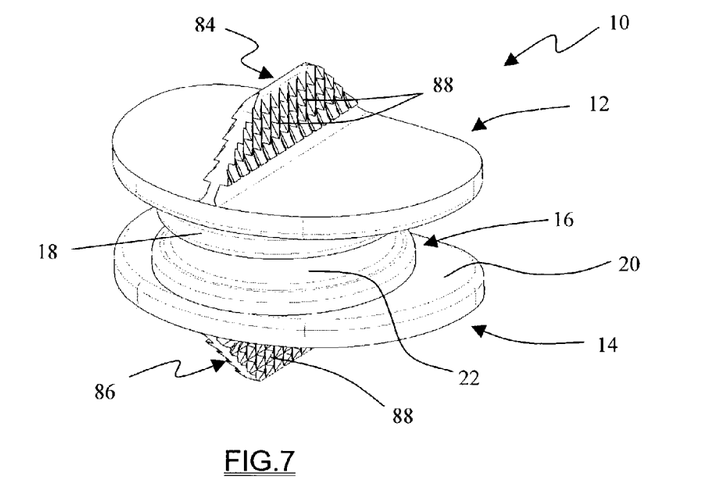
FIGS. 7-9 illustrate a total disc replacement system of "semi-constrained" translational construction according to still further aspect of the present invention.
Figure 8:
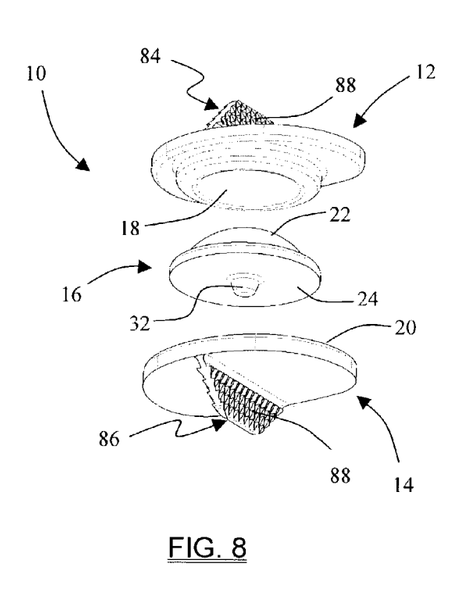
Figure 9:
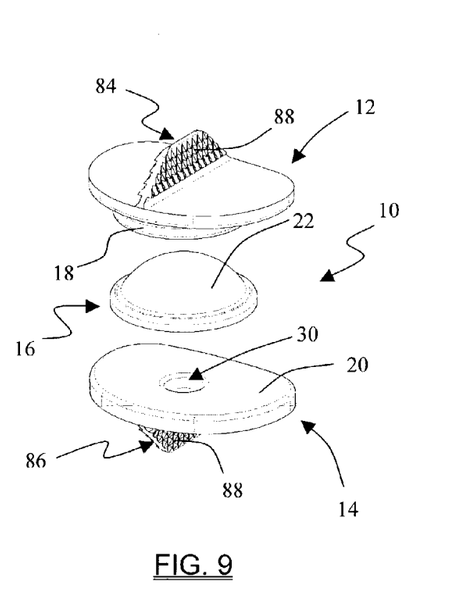

FIGS. 7-9 illustrate a TDR system 10 of "semi-constrained" translational construction according to still further aspect of the present invention. In this embodiment, the first anchor plate 12 is equipped with a generally concave receiving portion 18. The second anchor plate 14 has a generally flat surface 20 facing the generally concave receiving portion 18 of the first anchor plate 12 and includes a recess 30 in the approximate center thereof. The translating internal member 16 has a generally convex first surface 22 for engaging with the generally concave receiving portion 18 of the first anchor plate 12 and a generally flat second surface 24 for engaging with the generally flat surface 20 of the second anchor plate 14. In this embodiment, the translating internal member 16 also includes a post or rod element 32 for engaging within the recess 30 of the second anchor plate 14. When implanted and anchored into the vertebral bodies, this embodiment functions in essentially the same manner as that semi-constrained embodiment shown and described above with reference to FIGS. 4-6, except that the relative position of the post element 26 and the recess 28 is reversed.

Figure 10:
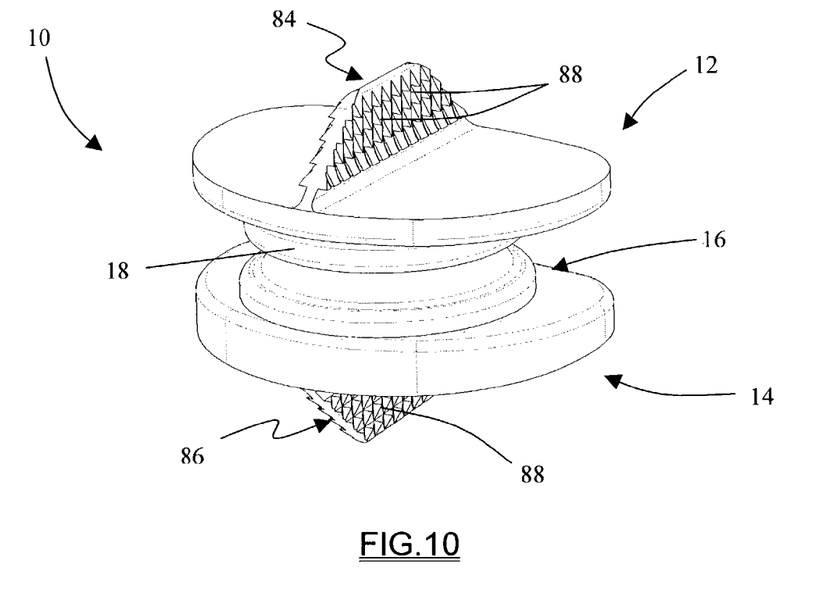
FIGS. 10-11 illustrate a total disc replacement system having at least one anchor plate of varying height to provide a non-parallel relationship between adjacent vertebral bodies (for lordosis or kyphosis) according to a still further aspect of the present invention.
Figure 11:
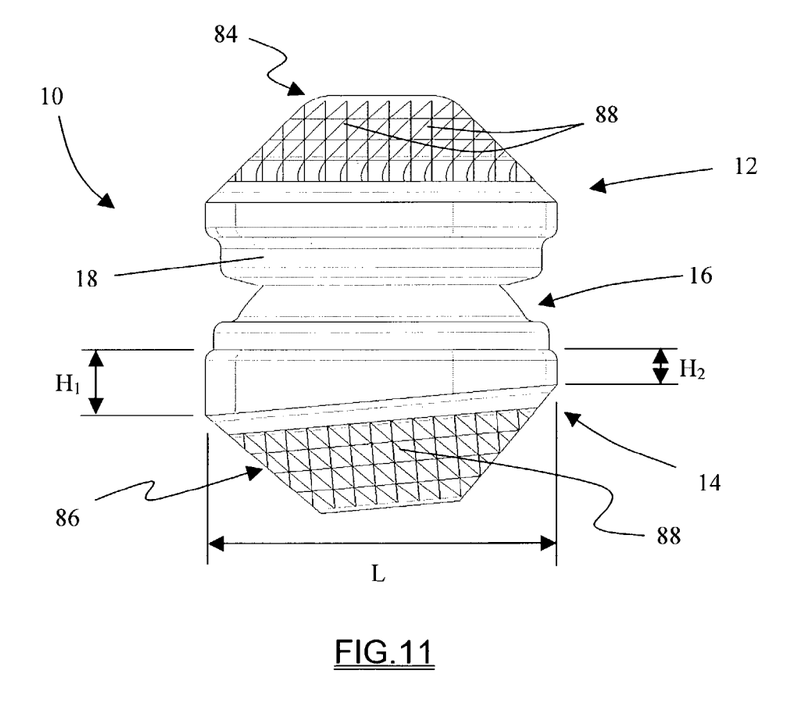

FIGS. 10-11 illustrate a TDR system 10 having at least one anchor plate of varying height to provide a non-parallel relationship between adjacent vertebral bodies according to a still further aspect of the present invention. This TDR system 10 is shown by way of example only as being of the same general construction as that shown and described with reference to FIGS. 1-9. The main distinction is that, in the embodiment of FIGS. 10-11, one or more of the anchor plates 12, 14 may be provided having a height that varies along a length of the anchor plate such that, when implanted, it forces the respective vertebral bodies into a non-parallel relationship to assume the intervertebral shape occurring in a particular region of the spine. For example, for lumbar and cervical applications, varying the height of the anchor plate(s) (lower posteriorly and higher anteriorly) may advantageously facilitate a lordotic relationship between adjacent vertebral bodies as found naturally in those regions of the spine. In similar fashion, for thoracic applications, varying the height of the anchor plate(s) higher posteriorly and lower anteriorly may advantageously facilitate a kyphotic relationship between adjacent vertebral bodies as found naturally in that region of the spine. As shown most clearly in FIG. 11, the second anchor plate 14 is (by way of example only) provided having a height that varies from height $H_1$ to $H_2$ along a length L. This angled or wedged characteristic of second anchor plate 14 causes the vertebral bodies in which the anchor plates 12, 14 are positioned to assume a natural lordotic or kyphotic relation when the TDR system 10 is implanted, depending upon the implantation site.

Figure 12:
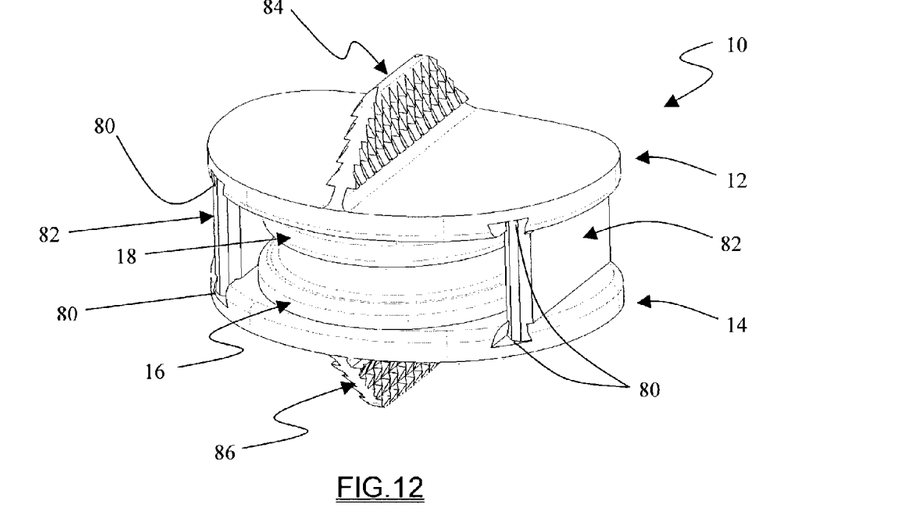
FIGS. 12-14 illustrate a total disc replacement system having post-implantation fusion capabilities according to yet another aspect of the present invention.
Figure 13:
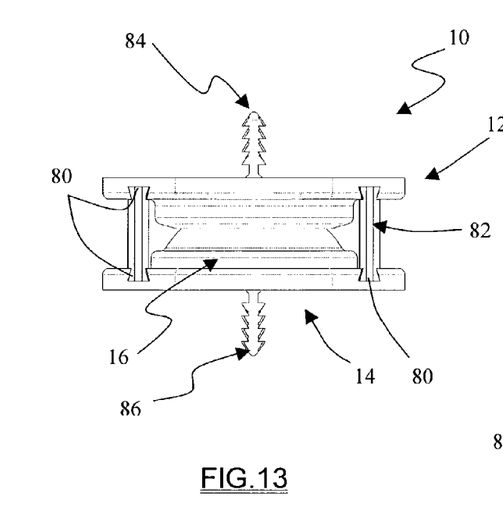
Figure 14:
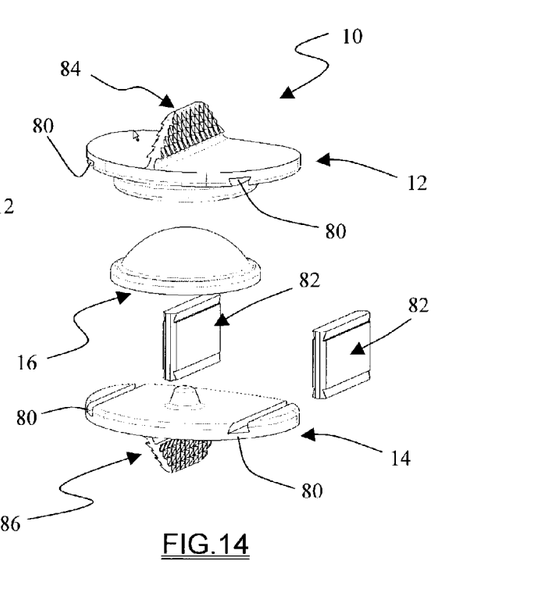

FIGS. 12-14 illustrate a TDR system 10 having post-implantation fusion capabilities according to yet another aspect of the present invention. In this important aspect of the present invention, any of the TDR systems 10 described herein or contemplated hereby (including those described in the prior art) may be provided such that the anchor plates 12, 14 may be locked in place relative to one another after implantation of the original TDR system 10, thereby effectively accomplishing fusion between the adjacent vertebral bodies. In one embodiment, this is accomplished by providing each anchor plate 12, 14 with engagement slots or grooves 80 on either side of the internal member 16 (or assembly 44), wherein strut members 82 can be introduced into (and fixed within) the slots 80 to effectively lock the relative position of the anchor plates 12, 14. This feature is advantageous in that it provides the ability to undertake the post-implantation corrective measure of spinal fusion without first removing the entire total disc replacement system 10. Moreover, this design capitalizes on the fact that the anchor plates 12, 14 will likely have an extremely robust and secure engagement to the vertebral bodies, in that any corrective measure may well take place months, if not years, after the initial implantation of the TDR device 10. By introducing the strut members 82 between the securely engaged anchor plates 12, 14, fusion can be accomplished immediately and without fear of complications that sometimes occur during traditional fusion techniques.

The introduction of the strut members 82 into the slots 80 may be facilitated by dimensioning these respective parts such that they mate in close engagement, such as by constructing the slots 80 as dove-tail female portions and the respective top and bottom edges of the struts 82 has dove-tail male portions. Any number of different mechanisms or techniques can be employed to rigidly engage the strut members 82 to anchor plates 12, 14, including but not limited to the use of adhesives or set screws within the slots 80. The strut members 82 may be constructed from any number of suitably rigid materials, including but not limited to metallic compositions or alloys, high-tensile strength plastics or compounds, or ceramics. The strut members 82 may also be constructed having a height that varies along the length of the strut member 82 such that, when fixed between the anchor plates 12, 14, it forces the respective vertebral bodies into a lordotic relationship as is found naturally in the spine. Although it may require distracting the adjacent vertebral bodies, it is nonetheless contemplated that the internal translating member 16 may be removed from between the anchor plates 12, 14 in order to receive a block member or some other structure capable of immobilizing the anchor plates 12, 14 relative to one another in order to effect fusion between the adjacent vertebral bodies.

According to a still further aspect of the present invention, any number of fixation techniques or features may be employed to secure the anchor plates 12, 14 to the respective vertebral bodies. FIGS. 1-14 illustrate a preferred fixation technique, wherein each anchor plate 12, 14 is equipped with a fin 84, 86 for securing the anchor plate 12, 14 to a respective vertebral endplate, such as by orienting the fins 84, 86 within slots formed in the vertebral body. In a still further preferred embodiment, as shown in FIGS. 1-14, the fins 84, 86 may include a plurality of projections 88 for resisting movement after implantation, thereby providing an additional anchoring mechanism to secure the anchor plates 12, 14 to the vertebral bodies.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as defined by the appended claims.

What is claimed is:

1. A method of fusing a first vertebral body to a second vertebral body, comprising:
    implanting a first member such that at least one first element extending from said first member is disposed within a first vertebral body;
    implanting a second member such that at least one second element extending from said second member is disposed within a second vertebral body;
    inserting at least one internal translating member such that said internal translating member is disposed between said first member and said second member, said internal translating member adapted to translate between said first and second members after implantation in a first surgery to preserve motion between said first and second vertebral bodies, wherein one of said second member and said internal translating member includes a post extending therefrom and the other of said second member and said internal translating member includes a recess configured to receive said post therein, said post having a diameter that is smaller than the diameter of said recess to allow for translation of said internal translating member; and
    selectively immobilizing said first member relative to said second member in a second surgery to prevent translation of said internal translating member and thereby effecting fusion between said first and second vertebral bodies.

2. The method of claim 1, wherein said first member and said second member are first and second anchor plates, respectively, of a total disc replacement system.

3. The method of claim 2, wherein said first anchor plate has a generally concave receiving portion.

4. The method of claim 3, wherein said second anchor plate has a generally flat surface facing said generally concave receiving portion of said first anchor plate.

5. The method of claim 4, wherein said post is positioned on said generally flat surface of said second anchor plate.

6. The method of claim 1, wherein at least one of said first and second element comprises an anchor fin dimensioned to be implanted within a slot formed within a vertebral body.

7. The method of claim 6, said anchor fin includes a plurality of projections for preventing the movement of said anchor fin after implantation.

8. The method of claim 1, wherein selectively immobilizing said first member relative to said second member comprises inserting at least one locking member adapted to immobilize said first member relative to said second member after implantation in said second surgery to prevent translation of said internal translating member and thereby effect fusion between adjacent vertebral bodies.

9. The method of claim 8, wherein said at least one locking member is a strut member capable of engagement between said first and second members.

10. The method of claim 9, wherein said strut member engages within slots formed in said first and second members.

11. A method of effecting fusion between adjacent vertebral bodies, comprising:
    implanting a total disc replacement system into an intervertebral space during a first surgery, said total disc replacement system comprising:
      a first anchor plate having a generally concave receiving portion;
      a second anchor plate having a generally flat surface facing said generally concave receiving portion of said first anchor plate; and
      an internal member having a generally convex first surface for engaging with said generally concave receiving portion of said first anchor plate, and a generally flat second surface for engaging with said generally flat surface of said second anchor plate, at least one of said generally convex first surface and said generally flat second surface adapted to translate relative to a respective one of said generally concave receiving portion of said first anchor plate and said generally flat surface of said second anchor plate after implantation in said first surgery to preserve motion between adjacent vertebral bodies, wherein one of said second anchor plate and said internal member includes a post extending therefrom and the other of said second anchor plate and said internal member includes a recess configured to receive said post therein, said post having a diameter that is smaller than the diameter of said recess; and
    immobilizing said first anchor plate relative to said second anchor plate by locking, during a second surgery, said first anchor plate to said second anchor plate to prevent relative movement between said first and second anchor plates.

12. The method of claim 11, wherein said total disc replacement system further includes at least one locking member adapted to immobilize said first anchor plate relative to said second anchor plate after implantation in said second surgery to prevent translation of said internal member and thereby effect fusion between adjacent vertebral bodies.

13. The method of claim 12, wherein said at least one locking member is a strut member capable of engagement between said first and second anchor plates.

14. The method of claim 13, wherein said strut member engages within slots formed in said first and second anchor plates.

15. The method of claim 11, wherein said first and second anchor plates each include an anchor fin for placement into a first and second vertebral body, respectively.

16. The method of claim 15, wherein each of said anchor fins includes a plurality of projections for preventing the movement of said anchor fins after implantation.

17. A method of fusing a first vertebral body to a second vertebral body, comprising:

implanting a first anchor plate of a total disc replacement system such that at least one first element extending from said first anchor plate is disposed within a first vertebral body, said first anchor plate having a generally concave receiving portion;

implanting a second anchor plate of a total disc replacement system such that at least one second element extending from said second anchor plate is disposed within a second vertebral body, said second anchor plate having a generally flat surface facing said generally concave receiving portion of said first anchor plate;

inserting at least one internal translating member such that said internal translating member is disposed between said first and second anchor plates, said internal translating member having a generally convex first surface for engaging with said generally concave receiving portion of said first anchor plate, and a generally flat second surface for engaging with said generally flat surface of said second anchor plate, at least one of said generally convex first surface and said generally flat second surface adapted to translate relative to a respective one of said generally concave receiving portion of said first anchor plate and said generally flat surface of said second anchor plate after implantation in said first surgery to preserve motion between adjacent vertebral bodies wherein one of said second anchor plate and said internal translating member includes a post extending therefrom and the other of said second anchor plate and said internal translating member includes a recess configured to receive said post therein, said post having a diameter that is smaller than the diameter of said recess; and selectively immobilizing said first anchor plate relative to said second anchor plate in a second surgery to prevent translation of said internal translating member and thereby effecting fusion between said first and second vertebral bodies.

18. The method of claim 17, wherein at least one of said first and second element comprises an anchor fin dimensioned to be implanted within a slot formed within a vertebral body.

19. The method of claim 18, said anchor fin includes a plurality of projections for preventing the movement of said anchor fin after implantation.

20. The method of claim 17, wherein selectively immobilizing said first anchor plate relative to said second anchor plate comprises inserting at least one locking member adapted to immobilize said first anchor plate relative to said second anchor plate after implantation in said second surgery to prevent translation of said internal translating member and thereby effect fusion between adjacent vertebral bodies.

21. The method of claim 20, wherein said at least one locking member is a strut member capable of engagement between said first and second anchor plates.

22. The method of claim 21, wherein said strut member engages within slots formed in said first and second anchor plates.

* * * * *